United States Patent [19]
Kasan et al.

[11] Patent Number: 4,889,724
[45] Date of Patent: Dec. 26, 1989

[54] STABLE AQUEOUS CISPLATIN SOLUTIONS

[75] Inventors: Rodney Kasan; Michael Seiffe, both of Raanana; Haim Yellin, Ramat-Gan, all of Israel

[73] Assignee: Teva Pharmaceutical Industries Ltd., Israel

[21] Appl. No.: 228,521

[22] Filed: Aug. 4, 1988

Related U.S. Application Data

[63] Continuation of Ser. No. 88,665, Aug. 24, 1987, abandoned.

[30] Foreign Application Priority Data

Jul. 30, 1987 [IL] Israel ......................................... 83380

[51] Int. Cl.$^4$ ............................................. A61K 33/24
[52] U.S. Cl. ..................................................... 424/649
[58] Field of Search ................................ 424/131, 649

[56] References Cited

FOREIGN PATENT DOCUMENTS 0143478  6/1985  European Pat. Off. ............ 424/131

Primary Examiner—Jerome D. Goldberg
Attorney, Agent, or Firm—Steinberg & Raskin

[57] ABSTRACT

Stable aqueous injectable Cisplatin solutions. The solutions comprise 0.1–1.0 mg/ml of Cisplatin, 9–15 mg/ml of NaCl and 0.025–0.075 mg/ml of citric acid. These solutions have the advantage of combining a mild pH range of 3.0–6.0 with a long shelf life.

6 Claims, No Drawings

STABLE AQUEOUS CISPLATIN SOLUTIONS

This is a continuation of application Ser. No. 088,665, filed 8/24/87, now abandoned.

FIELD OF INVENTION

The invention relates to a stable aqueous solution of Cisplatin.

The term "Cisplatin" as used hereinbelow refers to cis-diamminedichloroplatinum (II) of the following formula (I):

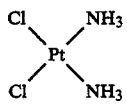

BACKGROUND OF THE INVENTION AND PRIOR ART

Cisplatin is known in its antineoplastic properties and is therefore widely used in chemotherapy of cancer.

Cisplatin in aqueous solution exhibits a high degree of instability which results in rapid decomposition of the complex. U.S. Pat. No. 4,310,515 discloses stable Cisplatin solutions, wherein the stability is achieved by a low pH in the range of 2-3 and the only means, disclosed therein for achieving such a low pH is by the use of hydrochloric acid (HCl).

The use of HCl creates several problems. For one, such a low pH is not well tolerated physiologically and it is painful when injected and even harmful when injected intramuscularly. Moreover, the use of concentrated HCl in the manufacturing procedure of the formulation is problematic.

SUMMARY OF THE INVENTION

In accordance with the present invention, it was unexpectedly found that a remarkably stable aqueous Cisplatin solution is obtained when the solution comprises citric acid and NaCl.

In accordance with the present invention, there is provided an injectable aqueous Cisplatin solution comprising 0.1-1.0 mg/ml of Cisplatin, 9-15 mg/ml of NaCl and 0.025-0.075 mg/ml of citric acid and having a pH of 3.0-6.0.

The pH of the Cisplatin solutions according to the invention is significantly higher than that of the above prior art solutions, which is of considerable advantage.

It has further been found that the Cisplatin solutions according to the invention have a long shelf life and do not decompose even after 3 years.

Preferably, the concentration of citric acid is about 0.05 mg/ml, that of NaCl is about 12 mg/ml and the pH of the solution is within the range of about 3.1–4.0. The most preferred pH of the Cisplatin solutions in accordance with the present invention is about 3.5.

Preferably, the Cisplatin concentration is either 1 mg/ml or 0.5 mg/ml in compliance with common requirements.

The Cisplatin solution in accordance with the present invention may be prepared in a conventional manner. Preparation of such a solution may, for example, be as follows:

An amount of sodium chloride is dissolved in approximately 80% of the final volume of freshly distilled water to yield the desired concentration, e.g. 12 mg/ml. Citric acid is added in an amount to yield a desired pH of about 3.5, which is achieved at a citric acid concentration of about 0.05 mg/ml. Cisplatin is then added to the solution and dissolved by vigorous stirring followed, if desired, by adjustment of the pH, e.g. by the addition of some amount of citric acid solution whereby the pH is lowered, or by the addition of some amount of a 1N NaOH solution whereby the pH is raised. Freshly distilled water is then added to the final volume.

For sterilization, the solution may be filtered, using, for example, a sterile 0.2 μm membrane filter under an atmosphere of a sterile 0.2 μm filtered dry nitrogen.

The Cisplatin solution so obtained may then be stored in appropriate containers, e.g. amber glass type I sterile vials of 10, 25, 50 and 100 ml, sealed with sterile chlorobutyl rubber stoppers and sealed with aluminum snap caps with inset polypropylene discs.

The so-prepared Cisplatin solutions were stored for various periods of time and at the end of each storage period, the solutions were tested, for pH and Cisplatin content. The Cisplatin content was determined using the high-pressure liquid chromotography method, BP 1980, Appendix III D p. A64 or USP XXI (621). Stainless steel columns of 25 cm long and 4 mm in inner diameter, prepacked with fine (10 μm diameter) particles of silica gel having a chemically bonded amino phase (the particles used were those known commercially as Lichrosorb NH$_2$). The eluent used in the chromotography consisted of a mixture of 1 volume of water and 19 volumes of acetone nitrile, and the flow rate was 1.5 ml/min. The Cisplatin in the ensuing solution was determined photometrically using an ultraviolet photometer set at a wavelength of 215 nm, fitted with a low-volume flow cell (8 μl). The results were compared with those for a standard Cisplatin solution containing Cisplatin at a concentration of 1 mg/ml and sodium chloride at a concentration of 0.9% (w/v).

Table 1 below demonstrates the remarkable stability over time of a 1 mg/ml Cisplatin solutions kept at room temperatures.

TABLE 1

| Storage time in months | Vial Volume (ml) | Content | pH |
|---|---|---|---|
| Initial | | 98.2 | 3.50 |
| 3 | 10 | 101.3 | 3.50 |
| 7 | 10 | 96.7 | 3.88 |
| 14 | 10 | 102.1 | 3.76 |
| | 25 | 99.5 | 3.63 |
| | 50 | 97.3 | 3.65 |
| | 100 | 99.0 | 3.57 |
| 20 | 10 | 100.5 | 3.91 |
| | 25 | 99.0 | 3.84 |
| | 50 | 99.6 | 3.78 |
| | 100 | 100.0 | 3.70 |
| 26 | 10 | 108.0 | 4.51 |
| 37 | 10 | 101.1 | 3.70 |
| 40 | 10 | 101.0 | 4.41 |
| 48 | 10 | 90.2 | 4.29 |

Table 2 demonstrates the stability of a 1 mg/ml Cisplatin solution kept at 37° C. It should be noted that the breakdown of Cisplatin at 37° C. is accelerated as compared to room temperature.

TABLE 2

CONTENT OF CISPLATIN AS % OF LABELED AMOUNT

| Storage time in months | Results | pH |
|---|---|---|
| Initial | 105.9 | 3.57 |
|  | 105.9 | 3.57 |
| 3 | 100.6 | 3.81 |
|  | 99.8 | 3.81 |
| 4 | 103.8 | 4.33 |
|  | 101.0 | 4.33 |
| 6 | 100.6 | 4.20 |
|  | 98.6 | 4.20 |
| 9 | 97.6 | 4.54 |
|  | 97.8 | 4.54 |
| 12 | 95.6 | 4.40 |
|  | 93.3 | 4.40 |

Table 3 demonstrates the stability of 0.5 mg/ml Cisplatin solution kept at 37° C.

TABLE 3

| Storage time in months | Results | pH |
|---|---|---|
| Initial | 105.0 | 3.53 |
|  | 105.1 | 3.53 |
| 1 | 101.6 | 3.72 |
|  | 98.8 | 3.72 |
|  | 98.1 | 3.82 |
|  | 98.7 | 3.82 |
| 2 | 100.3 | 3.73 |
|  | 99.3 | 3.73 |
|  | 101.3 | 3.83 |
|  | 101.3 | 3.83 |
| 3 | 105.9 | 3.60 |
|  | 106.0 | 3.60 |
|  | 106.0 | 3.90 |
|  | 106.7 | 3.90 |

We claim:

1. An aqueous injectable Cisplatin solution comprising 0.1–1.0 mg/ml of Cisplatin, 9–15 mg/ml of NaCl and 0.025–0.075 mg/ml of citric acid and having a pH of 3.0–6.0.

2. An injectable solution according to claim 1 wherein the NaCl concentration is about 12 mg/ml.

3. An injectable solution according to claim 1 or 2 wherein the citric acid concentration is about 0.05 mg/ml.

4. A solution according to claim 3 having a pH of about 3.5.

5. The solution of claim 1, having a pH of about 3.1–4.0.

6. The solution of claim 1, wherein said Cisplatinum concentration is either 1 mg/ml or 0.5 mg/ml.

* * * * *